(12) United States Patent
Santos et al.

(10) Patent No.: US 7,887,517 B2
(45) Date of Patent: Feb. 15, 2011

(54) DRUG CASTING

(75) Inventors: Cesario Dos Santos, Aliso Viejo, CA (US); Raffi Pinedjian, Fountain Valley, CA (US); Robert Sanchez, Oceanside, CA (US); Bruno Dacquay, Irvine, CA (US); Casey Lind, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 865 days.

(21) Appl. No.: 11/833,668

(22) Filed: Aug. 3, 2007

(65) Prior Publication Data

US 2008/0021413 A1      Jan. 24, 2008

Related U.S. Application Data

(63) Continuation-in-part of application No. 11/435,906, filed on May 17, 2006, now abandoned.

(60) Provisional application No. 60/921,497, filed on Oct. 16, 2006, provisional application No. 60/921,498, filed on Oct. 16, 2006, provisional application No. 60/921,499, filed on Oct. 16, 2006.

(51) Int. Cl.
*A61M 5/178* (2006.01)
(52) U.S. Cl. .................. 604/218; 264/212; 264/636
(58) Field of Classification Search ............. 604/60, 604/218; 264/478, 636, 212
See application file for complete search history.

(56) References Cited

U.S. PATENT DOCUMENTS

| | | | |
|---|---|---|---|
| 1,252,614 A | 1/1918 | Pieper | |
| 3,089,815 A | 5/1963 | Lieb et al. | |
| 3,608,549 A | 9/1971 | Merrill | |
| 3,892,537 A | 7/1975 | Gulati et al. | |
| 3,982,537 A | 9/1976 | Bucalo | |
| 4,007,742 A | 2/1977 | Banko | |
| 4,030,499 A | 6/1977 | Bucalo | |
| 4,054,138 A | 10/1977 | Bucalo | |
| 4,122,850 A | 10/1978 | Bucalo | |
| 4,184,510 A | 1/1980 | Murry et al. | |
| 4,246,932 A | 1/1981 | Raines | |

(Continued)

FOREIGN PATENT DOCUMENTS

EP       0348146 A1      12/1989

(Continued)

OTHER PUBLICATIONS

"Ultra™ 2800 Positive Displacement Dispenser"; 2004; EFD, Inc. Brochure XP 1104 vol. 11.10; 2 pages.

(Continued)

*Primary Examiner*—Kevin C Sirmons
*Assistant Examiner*—Deanna K Hall
(74) *Attorney, Agent, or Firm*—Kenneth D. Bassinger

(57) ABSTRACT

An injection device assembly includes a dispensing chamber housing and a plunger. The dispensing chamber housing is coupled to a needle. The dispensing chamber housing has an inner surface and an outer surface. The inner surface partially defines a dispensing chamber for holding a quantity of a substance. A dosage of a substance is cast into the dispensing chamber housing or cast onto a plunger that is inserted into the dispensing chamber housing.

4 Claims, 7 Drawing Sheets

U.S. PATENT DOCUMENTS

| | | | |
|---|---|---|---|
| 4,265,618 A | 5/1981 | Herskovitz et al. | |
| 4,357,136 A | 11/1982 | Herskovitz et al. | |
| 4,392,827 A | 7/1983 | Martin | |
| 4,474,752 A | 10/1984 | Haslam et al. | |
| 4,484,915 A | 11/1984 | Tartaglia | |
| 4,582,488 A | 4/1986 | Newman | |
| 4,684,344 A | 8/1987 | Brockway et al. | |
| 4,704,088 A | 11/1987 | Newman | |
| 4,713,446 A | 12/1987 | DeVore et al. | |
| 4,795,423 A | 1/1989 | Osterholm | |
| 4,830,855 A | 5/1989 | Stewart | |
| 4,992,045 A | 2/1991 | Beisel | |
| 5,066,276 A | 11/1991 | Wang | |
| 5,120,307 A | 6/1992 | Wang | |
| 5,328,481 A | 7/1994 | Wang | |
| 5,336,175 A | 8/1994 | Mames | |
| 5,360,413 A | 11/1994 | Leason et al. | |
| 5,370,630 A | 12/1994 | Smidebush et al. | |
| 5,474,535 A * | 12/1995 | Place et al. | 604/60 |
| 5,476,511 A | 12/1995 | Gwon et al. | |
| 5,487,725 A | 1/1996 | Peyman | |
| 5,582,595 A | 12/1996 | Haber et al. | |
| 5,620,700 A | 4/1997 | Berggren et al. | |
| 5,743,886 A | 4/1998 | Lynn et al. | |
| 5,773,019 A | 6/1998 | Ashton et al. | |
| 5,783,205 A | 7/1998 | Berggren et al. | |
| 5,824,072 A | 10/1998 | Wong | |
| 5,860,949 A | 1/1999 | Chen | |
| 5,928,663 A | 7/1999 | Peyman | |
| 5,984,889 A | 11/1999 | Christ et al. | |
| 6,079,765 A | 6/2000 | Zaguskin et al. | |
| 6,210,357 B1 | 4/2001 | Morris | |
| 6,270,343 B1 | 8/2001 | Martin | |
| 6,290,690 B1 | 9/2001 | Huculak et al. | |
| 6,364,865 B1 | 4/2002 | Lavi et al. | |
| 6,372,245 B1 | 4/2002 | Bowman et al. | |
| 6,413,245 B1 | 7/2002 | Yaacobi et al. | |
| 6,419,656 B1 | 7/2002 | Vetter et al. | |
| 6,436,143 B1 | 8/2002 | Ross et al. | |
| 6,488,659 B1 | 12/2002 | Rosenman | |
| 6,520,930 B2 | 2/2003 | Critchlow et al. | |
| 6,585,700 B1 | 7/2003 | Trocki et al. | |
| 6,595,979 B1 | 7/2003 | Epstein et al. | |
| 6,635,267 B1 | 10/2003 | Miyoshi et al. | |
| 6,645,179 B1 | 11/2003 | Ishikawa et al. | |
| 6,726,654 B2 | 4/2004 | Rosenman | |
| 6,940,209 B2 | 9/2005 | Henderson | |
| 6,991,457 B2 | 1/2006 | Kazen et al. | |
| 7,176,030 B2 | 2/2007 | Faries, Jr. et al. | |
| 2002/0055720 A1 | 5/2002 | Hohlfelder et al. | |
| 2003/0055380 A1 | 3/2003 | Flaherty | |
| 2003/0125665 A1 | 7/2003 | Rosenman | |
| 2004/0039253 A1 | 2/2004 | Peyman et al. | |
| 2004/0052761 A1 | 3/2004 | Vernon et al. | |
| 2004/0133155 A1 | 7/2004 | Varner et al. | |
| 2004/0176720 A1 | 9/2004 | Kipfer | |
| 2004/0210200 A1 | 10/2004 | Gerondale et al. | |
| 2004/0231667 A1 | 11/2004 | Horton et al. | |
| 2005/0065477 A1 | 3/2005 | Jost | |
| 2005/0177137 A1 | 8/2005 | Kipfer | |
| 2006/0079765 A1 | 4/2006 | Neer et al. | |

FOREIGN PATENT DOCUMENTS

| | | |
|---|---|---|
| EP | 0398394 | 11/1990 |
| GB | 1551767 | 8/1979 |
| WO | WO 82/03761 A1 | 11/1982 |
| WO | WO 87/00029 A1 | 1/1987 |
| WO | WO 96/03978 A1 | 2/1996 |
| WO | WO 96/37247 | 11/1996 |
| WO | WO 99/33853 A2 | 7/1999 |
| WO | WO 99/65548 | 12/1999 |
| WO | WO 01/10482 A1 | 2/2001 |
| WO | WO 2006/050008 A1 | 5/2006 |

OTHER PUBLICATIONS

"Parker: Your Resource For Motion And Fluid Control Components, Systems and Solutions—System Solutions For Life Sciences"; 2003; Aurora Instruments, LLC Brochure; 8 pages.

* cited by examiner

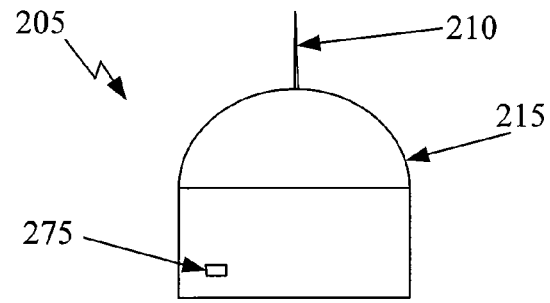
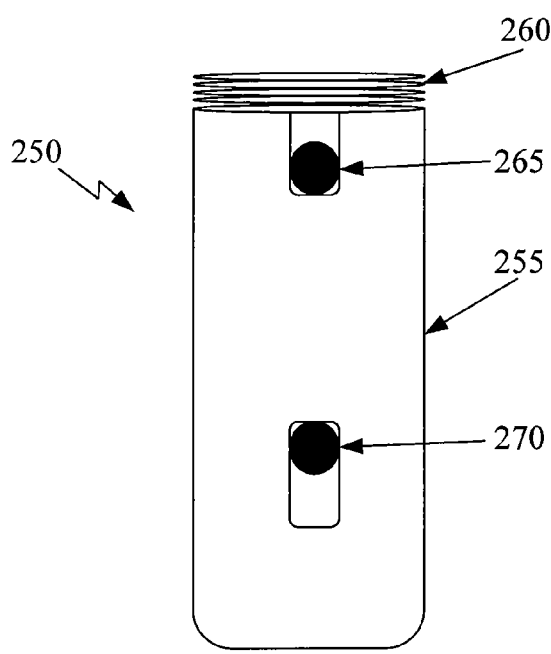
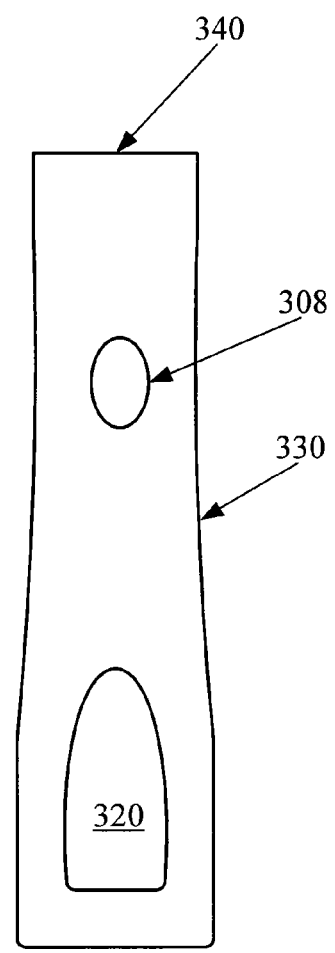
Fig. 2
Fig. 3

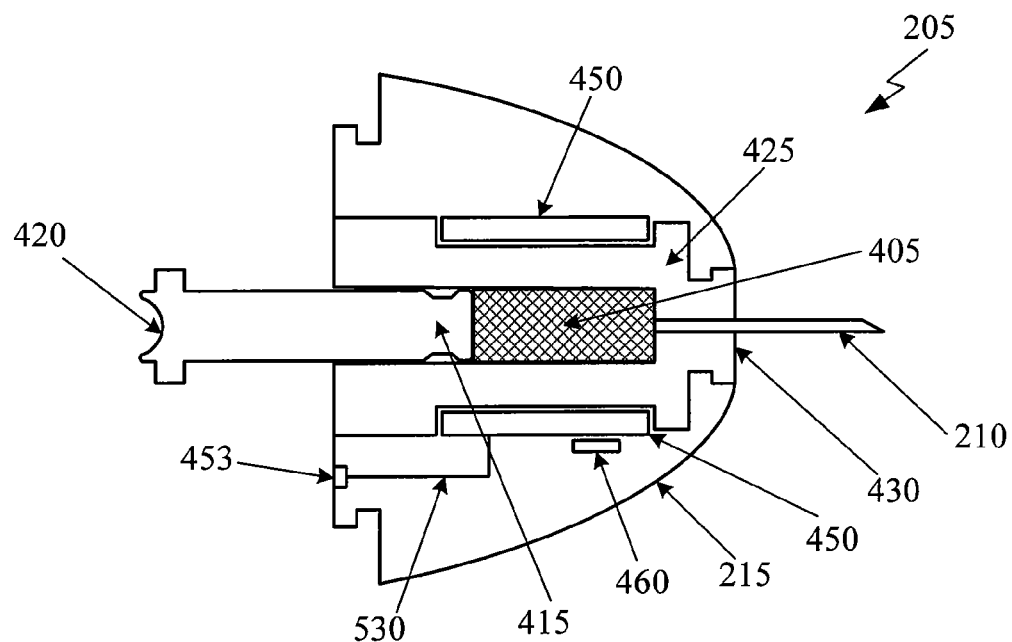
Fig. 5
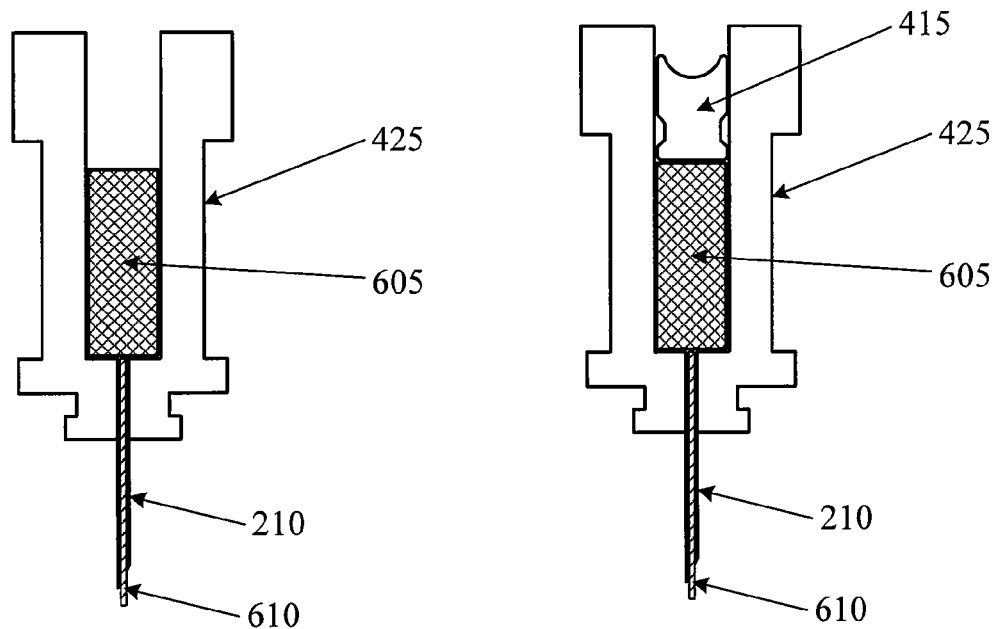
Fig. 6A  Fig. 6B

DRUG CASTING

RELATED APPLICATIONS

This Application claims priority to U.S. Patent Application No. 60/921,497 filed Oct. 16, 2006, U.S. Patent Application No. 60/921,498 filed Oct. 16, 2006 and U.S. Patent Application No. 60/921,499 filed Oct. 16, 2006, and is a continuation-in-part of U.S. patent application Ser. No. 11/435,906 filed May 17, 2006 now abandoned.

BACKGROUND OF THE INVENTION

The present invention relates to a medical device and more particularly to an injection device or subassembly thereof into which a drug has been cast.

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

These, and other diseases, can be treated by injecting a drug into the eye. Such injections are typically done manually using a conventional syringe and needle. FIG. 1 is a perspective view of a prior art syringe used to inject drugs into the eye. In FIG. 1, the syringe includes a needle 105, a luer hub 110, a chamber 115, a plunger 120, a plunger shaft 125, and a thumb rest 130. As is commonly known, the drug to be injected is located in chamber 115. Pushing on the thumb rest 130 causes the plunger 120 to expel the drug through needle 105.

In using such a syringe, the surgeon is required to pierce the eye tissue with the needle, hold the syringe steady, and actuate the syringe plunger (with or without the help of a nurse) to inject the fluid into the eye. The volume injected is typically not controlled in an accurate manner because reading the vernier is subject to parallax error. Fluid flow rates are uncontrolled. Tissue damage may occur due to an "unsteady" injection. Reflux of the drug may also occur when the needle is removed from the eye.

An effort has been made to control the delivery of small amounts of liquids. A commercially available fluid dispenser is the ULTRA™ positive displacement dispenser available from LFD Inc. of Providence, R.I. The ULTRA dispenser is typically used in the dispensing of small volumes of industrial adhesives. It utilizes a conventional syringe and a custom dispensing tip. The syringe plunger is actuated using an electrical stepper motor and an actuating fluid. Parker Hannifin Corporation of Cleveland, Ohio distributes a small volume liquid dispenser for drug discovery applications made by Aurora Instruments LLC of San Diego, Calif. The Parker/Aurora dispenser utilizes a piezo-electric dispensing mechanism. Ypsomed, Inc. of Switzerland produces a line of injection pens and automated injectors primarily for the self-injection of insulin or hormones by a patient. This product line includes simple disposable pens and electronically-controlled motorized injectors.

U.S. Pat. No. 6,290,690 discloses an ophthalmic system for injecting a viscous fluid (e.g. silicone oil) into the eye while simultaneously aspirating a second viscous fluid (e.g. perflourocarbon liquid) from the eye in a fluid/fluid exchange during surgery to repair a retinal detachment or tear. The system includes a conventional syringe with a plunger. One end of the syringe is fluidly coupled to a source of pneumatic pressure that provides a constant pneumatic pressure to actuate the plunger. The other end of the syringe is fluidly coupled to an infusion cannula via tubing to deliver the viscous fluid to be injected.

It would be desirable to have a portable handpiece for reliably injecting a drug into the eye. In the case where the drug is to be heated or cooled, it is often in a solid or semi-solid state at room temperature. It can be difficult to load such a drug into an injection device because of its viscosity. It would be desirable to bring the drug to a more liquid state and cast it into the injection device.

SUMMARY OF THE INVENTION

In one embodiment consistent with the principles of the present invention, the present invention is an injection device assembly having a dispensing chamber housing and a plunger. The dispensing chamber housing is coupled to a needle. The dispensing chamber housing has an inner surface and an outer surface. The inner surface partially defines a dispensing chamber for holding a quantity of a substance. The plunger is engaged with the inner surface of the dispensing chamber housing, is capable of sliding in the dispensing chamber housing, and is fluidly sealed to the inner surface of the dispensing chamber housing. The substance has been cast into the dispensing chamber housing.

In another embodiment consistent with the principles of the present invention, the present invention is an injection device assembly having a dispensing chamber housing and a plunger. The dispensing chamber housing is coupled to a needle. The dispensing chamber housing has an inner surface and an outer surface. The inner surface partially defines a dispensing chamber for holding a quantity of a substance. The plunger is engaged with the inner surface of the dispensing chamber housing, is capable of sliding in the dispensing chamber housing, and is fluidly sealed to the inner surface of the dispensing chamber housing. The substance has been cast onto the plunger prior to the plunger being inserted into the dispensing chamber housing.

In another embodiment consistent with the principles of the present invention, the present invention is a dosing assembly having a plunger with a top and bottom surface, and a removable sleeve. The removable sleeve has an interior and exterior surface and fits over the top surface of the plunger. In this position, the interior surface of the sleeve forms a mold into which a substance is cast onto the top surface of the plunger.

In another embodiment consistent with the principles of the present invention, the present invention is a dosing assembly having a dispensing chamber housing and a removable plug. The dispensing chamber housing is coupled to a needle. The dispensing chamber housing has an inner surface and an outer surface. The inner surface partially defines a dispensing chamber for holding a quantity of a substance. The removable plug is located in the needle and prevents the substance from exiting the dispensing chamber housing. The substance is cast into the dispensing chamber housing.

In another embodiment consistent with the principles of the present invention, the present invention is a method of dosing an injection device assembly comprising bringing a substance to a temperature range at which the substance is in a more liquid state; casting the substance into a dispensing chamber housing where the substance reverts to a more solid state; and inserting a plunger into the dispensing chamber housing.

In another embodiment consistent with the principles of the present invention, the present invention is a method of dosing an injection device assembly comprising bringing a substance to a temperature range at which the substance is in a more liquid state; placing a sleeve around a plunger; casting the substance into the sleeve and on top of the plunger where the substance reverts to a more solid state; removing the sleeve; and inserting the plunger and the substance into a dispensing chamber housing.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying figures, which are incorporated in and constitute a part of this specification, illustrate several embodiments of the invention and together with the description, serve to explain the principles of the invention.

FIG. 2 is one view of an ophthalmic medical device including a disposable tip segment and a limited reuse assembly according to an embodiment of the present invention.

FIG. 3 is another embodiment of a limited reuse assembly according to the principles of the present invention.

FIG. 5 is an exploded cross section view of a tip segment for an ophthalmic medical device according to an embodiment of the present invention.

FIGS. 6A and 6B are cross section views of a dispensing chamber with a drug that has been cast into it according to the principles of the present invention.

DETAILED DESCRIPTION OF THE PREFERRED EMBODIMENTS

Figure 1:
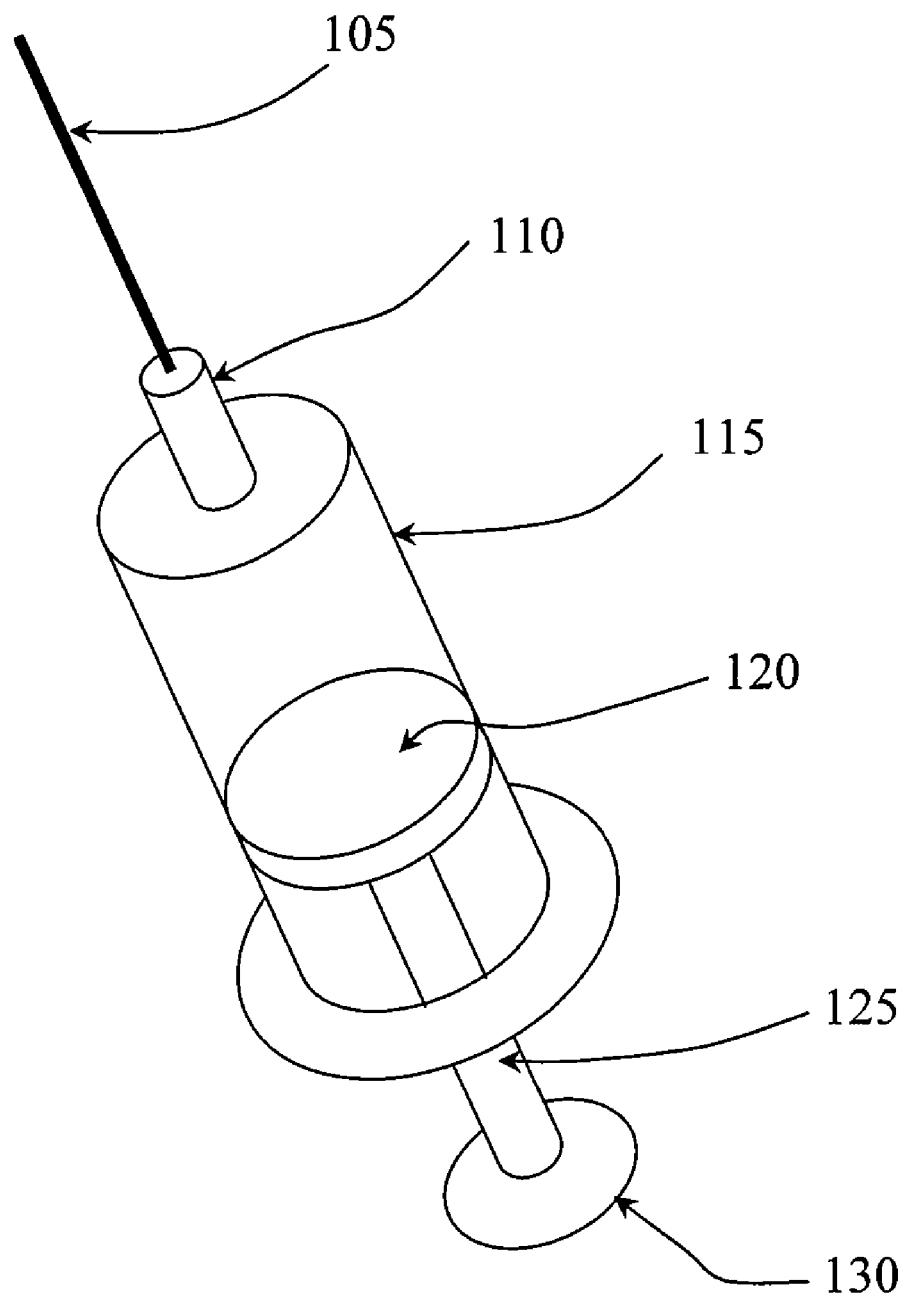
FIG. 1 is a perspective view of a prior art syringe.

Reference is now made in detail to the exemplary embodiments of the invention, examples of which are illustrated in the accompanying drawings. Wherever possible, the same reference numbers are used throughout the drawings to refer to the same or like parts.

FIG. 2 is one view of an ophthalmic medical device including a disposable tip segment and a limited reuse assembly according to an embodiment of the present invention. In FIG. 2, the medical device includes a tip segment 205 and a limited reuse assembly 250. The tip segment 205 includes a needle 210, a housing 215, and an optional light 275. The limited reuse assembly 250 includes a housing 255, a switch 270, a lock mechanism 265, and a threaded portion 260.

Tip segment 205 is capable of being connected to and removed from limited reuse assembly 250. In this embodiment, tip segment 205 has a threaded portion on an interior surface of housing 215 that screws onto the threaded portion 260 of limited reuse assembly 250. In addition, lock mechanism 265 secures tip segment 215 to limited reuse assembly 250. Lock mechanism 265 may be in the form of a button, a sliding switch, or a cantilevered mechanism. Other mechanisms for connecting tip segment 205 to limited reuse assembly 250, such as those involving structural features that mate with each other, are commonly known in the art and are within the scope of the present invention.

Needle 210 is adapted to deliver a substance, such as a drug, into an eye. Needle 210 may be of any commonly known configuration. Preferably, needle 210 is designed such that its thermal characteristics are conducive to the particular drug delivery application. For example, when a heated drug is to be delivered, needle 210 may be relatively short (several millimeters) in length to facilitate proper delivery of the drug.

Switch 270 is adapted to provide an input to the system. For example, switch 270 may be used to activate the system or to turn on a heater. Other switches, buttons, or user-directed control inputs are commonly known and may be employed with limited reuse assembly 250 and/or tip segment 205.

Optional light 275 is illuminated when tip segment 205 is ready to be used. Optional light 275 may protrude from housing 215, or it may be contained within housing 215, in which case, optional light 275 may be seen through a clear portion of housing 215. In other embodiments, optional light 275 may be replaced by an indicator, such as a liquid crystal display, segmented display, or other device that indicates a status or condition of disposable tip segment 205. For example, optional light 275 may also pulse on and off to indicate other states, such as, but not limited to a system error, fully charged battery, insufficiently charged battery or faulty connection between the tip segment 205 and limited use assembly 250. While shown on tip segment 205, optional light 275 or other indicator may be located on limited reuse assembly 250.

FIG. 3 is another embodiment of a limited reuse assembly according to the principles of the present invention. Limited reuse assembly 250 includes a button 308, a display 320, and a housing 330. Disposable tip segment 205 attaches to end 340 of limited reuse assembly 250. Button 308 is actuated to provide an input to the system. As with switch 270, button 308 may activate a heater or other temperature control device or initiate actuation of a plunger. Display 320 is a liquid crystal display, segmented display, or other device that indicates a status or condition of disposable tip segment 205 or limited reuse assembly 250.

Figure 4:
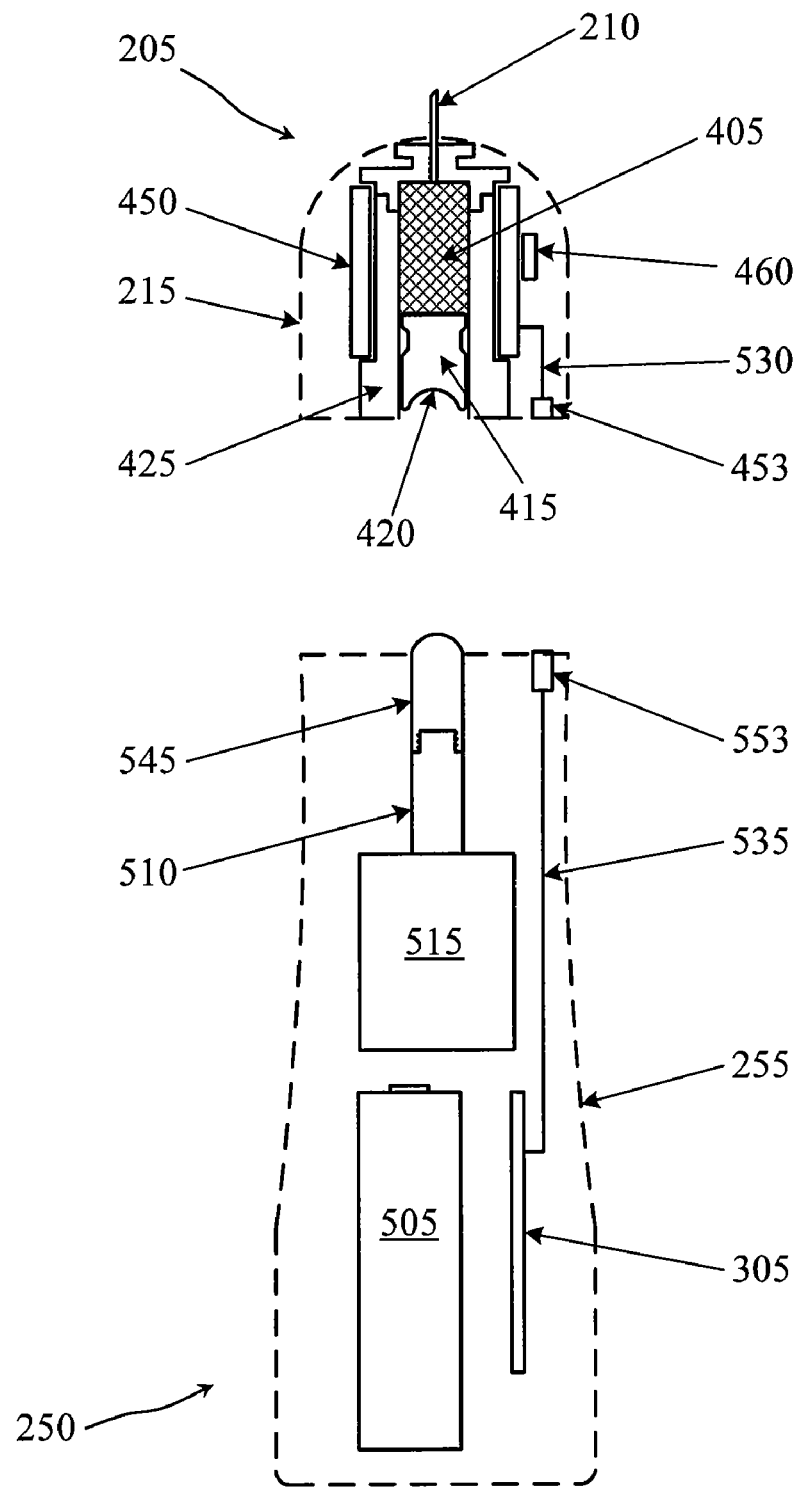
FIG. 4 is a cross section view of a disposable tip segment and a limited reuse assembly according to an embodiment of the present invention.

FIG. 4 is cross section view of a disposable tip segment and a limited reuse assembly according to an embodiment of the present invention. FIG. 4 shows how tip segment 205 interfaces with limited reuse assembly 250. In the embodiment of FIG. 4, tip segment 205 includes plunger interface 420, plunger 415, dispensing chamber housing 425, tip segment housing 215, temperature control device 450, thermal sensor 460, needle 210, dispensing chamber 405, interface 530, and tip interface connector 453. Limited reuse assembly 250 includes mechanical linkage interface 545, actuator shaft 510, actuator 515, power source 505, controller 305, limited reuse assembly housing 255, interface 535, and limited reuse assembly interface connector 553.

In tip segment 205, plunger interface 420 is located on one end of plunger 415. The other end of plunger 415 forms one end of dispensing chamber 405. Plunger 415 is adapted to slide within dispensing chamber 405. The outer surface of plunger 415 is fluidly sealed to the inner surface of dispensing chamber housing 425. Dispensing chamber housing 425 surrounds the dispensing chamber 405. Typically, dispensing chamber housing 425 has a cylindrical shape. As such, dispensing chamber 405 also has a cylindrical shape.

Needle 210 is fluidly coupled to dispensing chamber 405. In such a case, a substance contained in dispensing chamber 405 can pass through needle 210 and into an eye. Temperature control device 450 at least partially surrounds dispensing chamber housing 425. In this case, temperature control device 450 is adapted to heat and/or cool dispensing chamber housing 425 and any substance contained in dispensing chamber 405. Interface 530 connects temperature control device 450 with tip interface connector 453.

Optional thermal sensor 460 provides temperature information to assist in controlling the operation of temperature control device 450. Thermal sensor 460 may be located near dispensing chamber housing 425 and measure a temperature near dispensing chamber housing 425 or may be located in thermal contact with dispensing chamber housing 425, in which case it measures a temperature of dispensing chamber housing 425. Thermal sensor 460 may be any of a number of different devices that can provide temperature information. For example, thermal sensor 460 may be a thermocouple or a resistive device whose resistance varies with temperature. Thermal sensor is also electrically coupled to interface 530 or other similar interface.

The components of tip segment 205, including dispensing chamber housing 425, temperature control device 450, and plunger 415 are at least partially enclosed by tip segment housing 215. In one embodiment consistent with the principles of the present invention, plunger 415 is sealed to the interior surface of dispensing chamber housing 425. This seal prevents contamination of any substance contained in dispensing chamber 405. For medical purposes, such a seal is desirable. This seal can be located at any point on plunger 415 or dispensing chamber housing 425.

In limited reuse assembly 250, power source 505 provides power to actuator 515. An interface (not shown) between power source 505 and actuator 515 serves as a conduit for providing power to actuator 515. Actuator 515 is connected to actuator shaft 510. When actuator 515 is a stepper motor, actuator shaft 510 is integral with actuator 515. Mechanical linkage interface 545 is connected to actuator shaft 510. In this configuration, as actuator 515 moves actuator shaft 510 upward toward needle 210, mechanical linkage interface 545 also moves upward toward needle 210. In other embodiments of the present invention, mechanical linkage interface 545 and actuator shaft 510 are a single component. In other words, a shaft connected to actuator 515 includes both actuator shaft 510 and mechanical linkage interface 545 as a single assembly.

In limited reuse assembly 250, power source 505 is typically a rechargeable battery, such as a lithium ion battery, although other types of batteries may be employed. In addition, any other type of power cell is appropriate for power source 505. Power source 505 provides current to dispensing chamber housing 425 to heat it and change its shape. Optionally, power source 505 can be removed from housing 255 through a door or other similar feature (not shown).

Controller 305 is connected via interface 535 to limited reuse assembly interface connecter 553. Limited reuse assembly interface connecter 553 is located on a top surface of limited reuse assembly housing 255 adjacent to mechanical linkage interface 545. In this manner, both limited reuse assembly interface connector 553 and mechanical linkage interface 545 are adapted to be connected with tip interface connector 453 and plunger interface 420, respectively.

Controller 305 and actuator 515 are connected by an interface (not shown). This interface (not shown) allows controller 305 to control the operation of actuator 515. In addition, an interface between power source 505 and controller 305 allows controller 305 to control operation of power source 505. In such a case, controller 305 may control the charging and the discharging of power source 505 when power source 505 is a rechargeable battery.

Controller 305 is typically an integrated circuit with power, input, and output pins capable of performing logic functions. In various embodiments, controller 305 is a targeted device controller. In such a case, controller 305 performs specific control functions targeted to a specific device or component, such as a temperature control device or a power supply. For example, a temperature control device controller has the basic functionality to control a temperature control device. In other embodiments, controller 305 is a microprocessor. In such a case, controller 305 is programmable so that it can function to control more than one component of the device. In other cases, controller 305 is not a programmable microprocessor, but instead is a special purpose controller configured to control different components that perform different functions. While depicted as one component in FIG. 5, controller 305 may be made of many different components or integrated circuits.

Tip segment 205 is adapted to mate with or attach to limited reuse assembly 250. In the embodiment of FIG. 4, plunger interface 420 located on a bottom surface of plunger 415 is adapted to mate with mechanical linkage interface 545 located near a top surface of limited reuse assembly housing 255. In addition, tip interface connector 453 is adapted to connect with limited reuse assembly interface connector 553. When tip segment 205 is connected to limited reuse assembly 250 in this manner, actuator 515 and actuator shaft 510 are adapted to drive plunger 415 upward toward needle 210. In addition, an interface is formed between controller 305 and temperature control device 450. A signal can pass from controller 305 to temperature control device 450 through interface 535, limited reuse assembly interface connector 553, tip interface connector 453, and interface 530.

In operation, when tip segment 205 is connected to limited reuse assembly 250, controller 305 controls the operation of actuator 515. When actuator 515 is actuated, actuator shaft 510 is moved upward toward needle 210. In turn, mechanical linkage interface 545, which is mated with plunger interface 420, moves plunger 415 upward toward needle 210. A substance located in dispensing chamber 405 is then expelled through needle 210.

In addition, controller 305 controls the operation of temperature control device 450. Temperature control device 450 is adapted to heat and/or cool dispensing chamber housing 425 and its contents. Since dispensing chamber housing 425 is at least partially thermally conductive, heating or cooling dispensing chamber housing 425 heats or cools a substance located in dispensing chamber 405. Temperature information can be transferred from thermal sensor 460 through interface 530, tip interface connector 453, limited reuse assembly interface connector 553, and interface 535 back to controller 305. This temperature information can be used to control the operation of temperature control device 450. When temperature control device 450 is a heater, controller 305 controls the amount of current that is sent to temperature control device 450. The more current sent to temperature control device 450, the hotter it gets. In such a manner, controller 305 can use a feed back loop utilizing information from thermal sensor 460 to control the operation of temperature control device 450. Any suitable type of control algorithm, such as a proportional integral derivative (PID) algorithm, can be used to control the operation of temperature control device 450.

A substance to be delivered into an eye, typically a drug suspended in a phase transition compound, is located in dispensing chamber 405. In this manner, the drug and phase transition compound are contacted by the inner surface of dispensing chamber housing 425. The phase transition compound is in a solid or semi-solid state at lower temperatures and in a more liquid state at higher temperatures. Such a compound can be heated by the application of current to temperature control device 450 to a more liquid state and injected into the eye where it forms a bolus that erodes over time.

Likewise, a reverse gelation compound may be used. A reverse gelation compound is in a solid or semi-solid state at higher temperatures and in a more liquid state at lower temperatures. Such a compound can be cooled by temperature control device 450 to a more liquid state and injected into the eye where it forms a bolus that erodes over time. As such, temperature control device 450 may be a device that heats a substance in dispensing chamber 405 or a device that cools a substance in dispensing chamber 405 (or a combination of both). After being delivered into the eye, a phase transition compound or reverse gelation compound erodes over time providing a quantity of drug over an extended period of time. Using a phase transition compound or reverse gelation compound provides better drug dosage with fewer injections.

In one embodiment of the present invention, the substance located in dispensing chamber 405 is a drug that is preloaded into the dispensing chamber. In such a case, tip segment 205 is appropriate as a single use consumable product. Such a disposable product can be assembled at a factory with a dosage of a drug installed.

While shown as a two-piece device, the injection system of FIG. 4 may be a single piece device. In such a case, the tip segment is integrated into the limited reuse assembly to form a single medical device.

FIG. 5 is a cross section view of a tip segment for an ophthalmic medical device according to an embodiment of the present invention. In FIG. 5, tip segment 205 includes dispensing chamber housing 425, tip segment housing 215, thermal sensor 460, needle 210, dispensing chamber 405, plunger 415, plunger interface 420, temperature control device 450, interface 530, tip interface connector 453, and an optional luer 430. Optional luer secures needle 210 to dispensing chamber 425.

In the embodiment of FIG. 5, temperature control device 450 is activated to bring a substance in dispensing chamber 405 to within a proper temperature range. Thermal sensor 460 provides temperature information to controller 305 (not shown) to control temperature control device 450. After the substance has reached the proper temperature range, plunger 415 is actuated to deliver the substance through needle 210 and into an eye. Plunger 415 is extended and includes an integral shaft as shown.

FIGS. 6A and 6B are cross section views of a dispensing chamber with a drug that has been cast into it according to the principles of the present invention. In FIG. 6A, a drug suspended in a phase transition compound 605 has been heated and poured or cast into dispensing chamber housing 425 where it cools and solidifies. Plug 610 is located in needle 210 to prevent the drug suspended in a phase transition compound 605 from exiting through needle 210 when it is in a liquid or semi-liquid state. After the drug suspended in a phase transition compound 605 is cast into dispensing chamber housing 425, plunger 415 is inserted as shown in FIG. 6B.

Casting the drug suspended in a phase transition compound 605 into dispensing chamber housing 425 allows for small gauge needles to be used. In one embodiment according to the principles of the present invention, a 25 gauge needle is used. Loading a drug suspended in a phase transition compound 605 into dispensing chamber housing 425 through a small gauge needle is difficult. In addition, handling the phase transition compound at room temperature, when it is in a more solid wax-like form, can also be difficult. Loading such a material into an injection device when it is in a more solid form may lead to entrapment of air, imprecise dosage, and the like. "Melting" the substance and pouring it into dispensing chamber housing 425 provides an easier way of including the proper dosage in a pre-loaded injection device.

A drug suspended in a reverse gelation compound may also be employed. In such a case, the drug suspended in the reverse gelation compound is cooled until it becomes more liquid and is then cast into dispensing chamber housing 425 where it warms and solidifies.

Figures 7A, 7B, 7C, 7D:
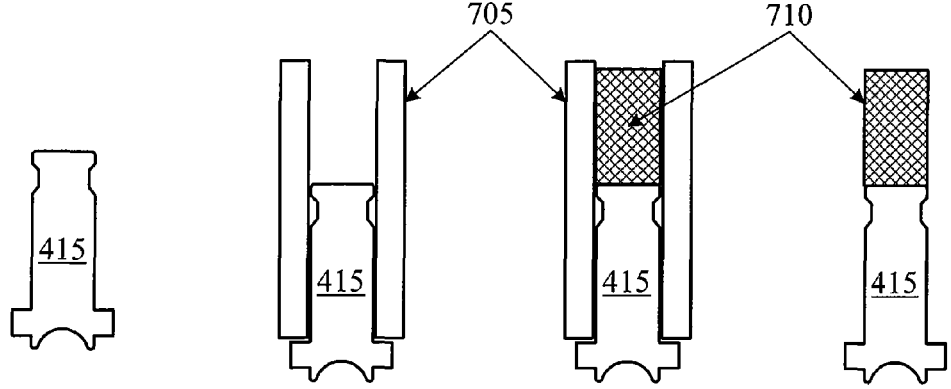
FIGS. 7A-7D are cross section views of a plunger with a drug that has been cast onto it according to the principles of the present invention.

FIGS. 7A-7D are cross section views of a plunger with a drug that has been cast onto it according to the principles of the present invention. FIG. 7A depicts a plunger. In FIGS. 7B and 7C, a sleeve 705 is placed around plunger 415 and a drug suspended in a phase transition or reverse gelation compound 710 is cast into sleeve 705 on top of plunger 415. Sleeve 705 has an interior and an exterior surface. The interior surface receives the substance. As the substance returns to room temperature, it solidifies and sleeve 705 is removed. Sleeve 705 may be hinged or its interior surface coated to allow for it to be removed. Sleeve 705 may also have guides (not shown) to allow it to be properly placed over the plunger. As shown in FIG. 7D, after sleeve 705 is removed, plunger 415 has the drug and compound 710 formed on top of it. Plunger 415 is then ready to be placed in dispensing chamber housing 425. Such a casting operation provides for ease of assembly for a preloaded injection device.

Figures 8A, 8B, 8C, 8D, 8E:
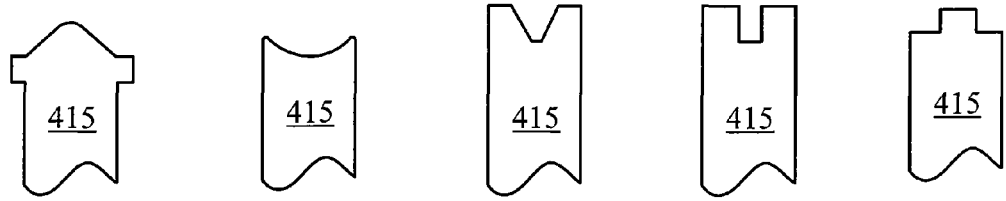
FIGS. 8A-8G are cross section views of various plungers according to the principles of the present invention.
Figures 8F, 8G, 9A, 9B:
FIGS. 9A and 9B are end views of various plungers according to the principles of the present invention.

FIGS. 8A-8G are cross section views of various plungers according to the principles of the present invention. Different plunger configurations can be utilized with the casting operation described in FIGS. 7A-7D. In some cases, it is desirable to provide a shape or texture on the top face of plunger 415. Such a shape or texture allows the cast drug and compound to better adhere to plunger 415. Better adherence allows for easier assembly of a pre-dosed injection device. In particular, in FIGS. 8A-8E the top face of plunger 415 has a particular shape. In FIG. 8F, the top face of plunger 415 is flat, and in FIG. 8G, it is textured.

FIGS. 9A and 9B are top views of various plungers according to the principles of the present invention. In FIG. 9A, three small holes or indentations are present in the top face of plunger 415. In FIG. 9B, a single hole or depression is present in the top face of plunger 415. Numerous other plunger configurations are possible, and those provided herein are merely examples.

Figure 10:
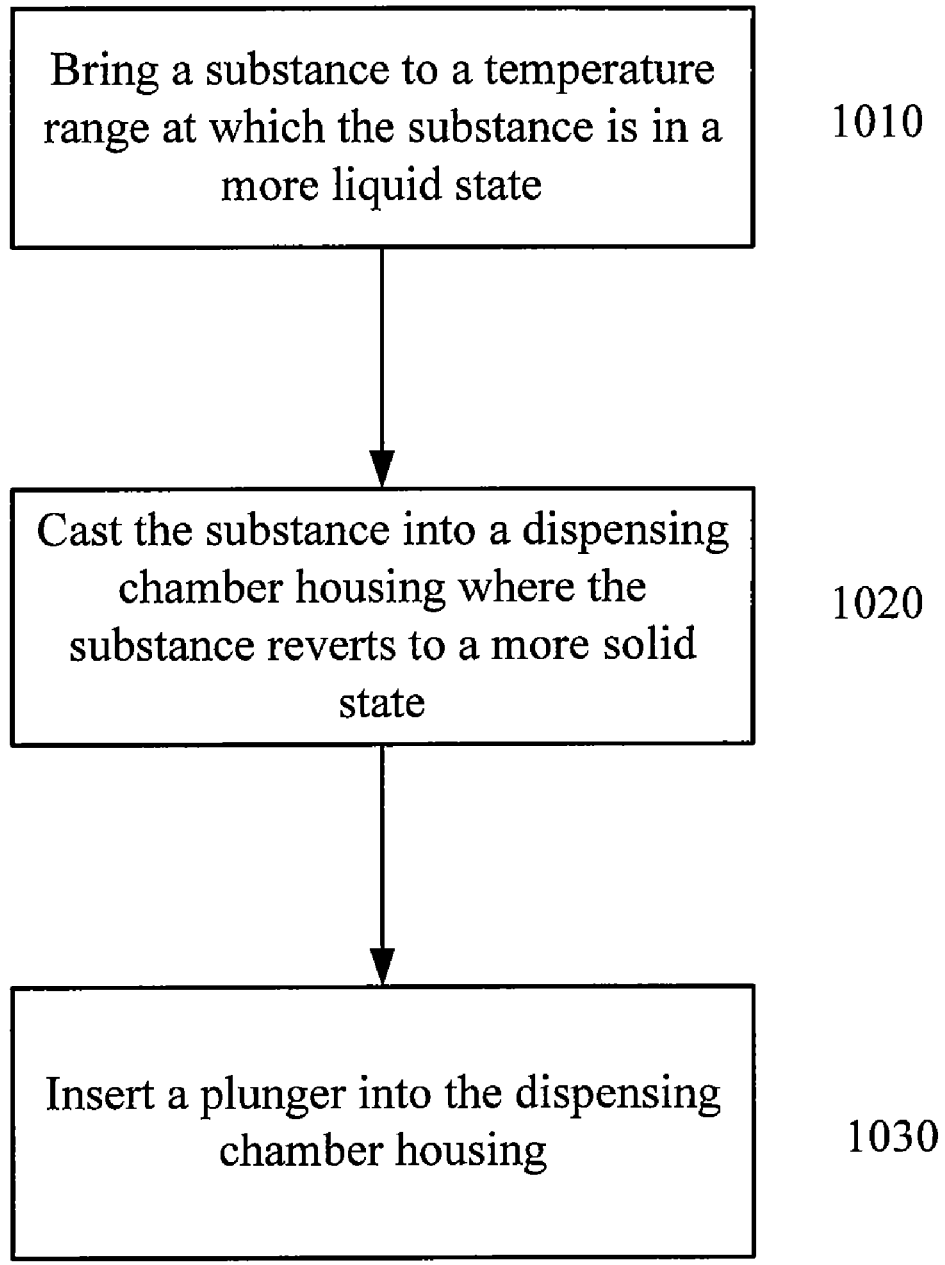
FIG. 10 is a flow chart of a method of casting a substance into an injection device or subassembly thereof according to the principles of the present invention.

FIG. 10 is a flow chart of a method of casting a substance into an injection device or subassembly thereof according to the principles of the present invention. In 1010, the substance is brought to a temperature range at which the substance is in a more liquid state. For a phase transition substance, heat is applied to bring it to a more liquid state. In 1020, the substance is cast into a dispensing chamber housing. A plug is located in the needle that is fluidly coupled to the dispensing chamber housing. The plug prevents the substance from exiting the dispensing chamber housing through the needle when the substance is in a more liquid state. After the substance is cast into the dispensing chamber housing, the substance gradually approaches room temperature and becomes more solid. In 1030, a plunger is inserted into the dispensing chamber housing. The injection device is then ready to be shipped to a medical professional for use. When the substance is a drug for treating a condition of the eye, a precise dosage can be cast into the dispensing chamber housing under sterile conditions at a manufacturing site. The pre-dosed injection device (with a precise dosage) can then be put in a sterile pack for shipment. Such a manufacturing process provides for accurate dosing of difficult substances in a controlled environment.

Figure 11:
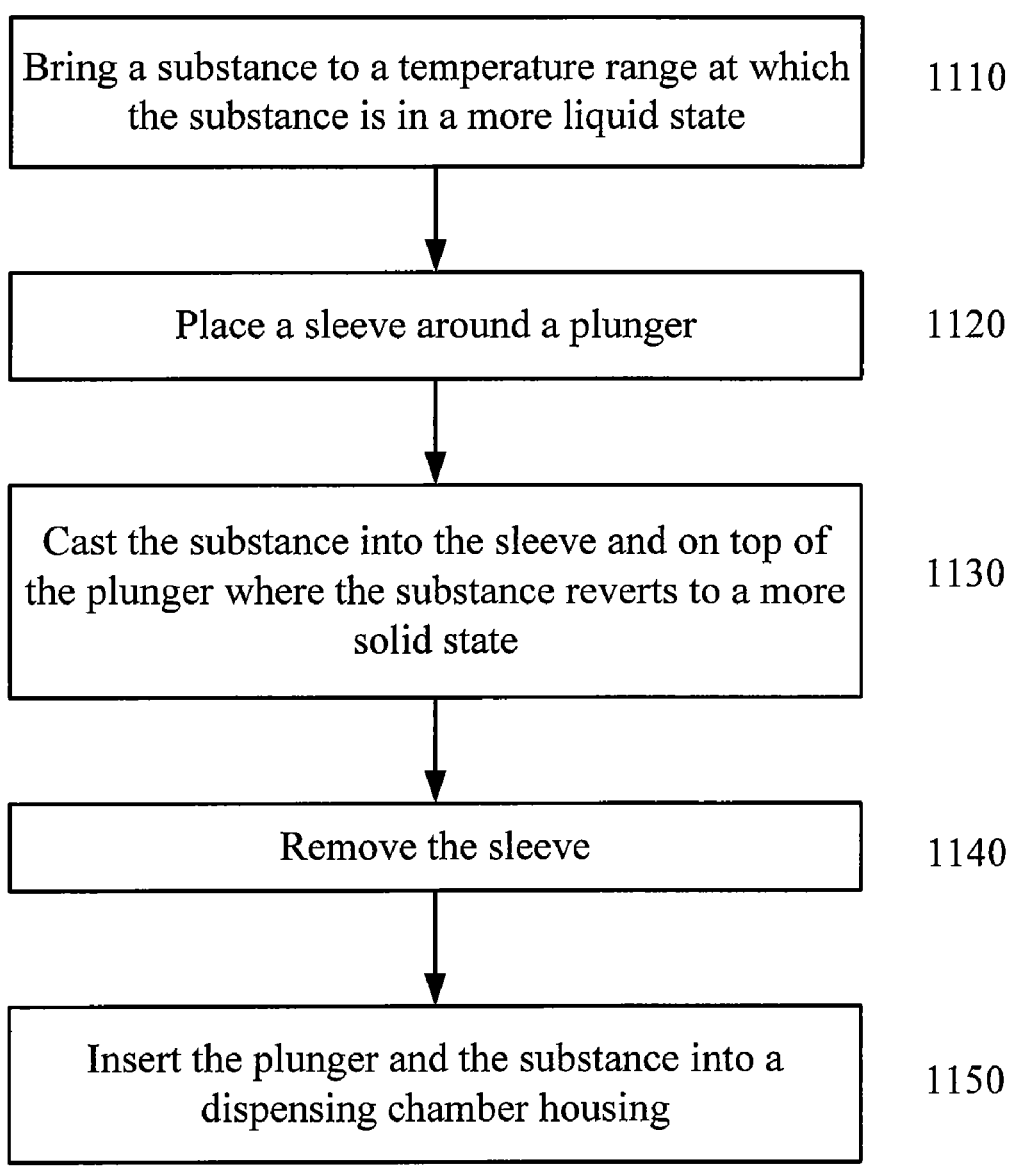
FIG. 11 is a flow chart of a method of casting a substance into an injection device or subassembly thereof according to the principles of the present invention.

FIG. 11 is a flow chart of a method of casting a substance into an injection device or subassembly thereof according to the principles of the present invention. In 1110, the substance is brought to a temperature range at which the substance is in a more liquid state. For a phase transition substance, heat is applied to bring it to a more liquid state. In 1120, a sleeve is placed around the top of a plunger. The sleeve forms a mold into which the substance can be cast. As such, the interior surface of the sleeve and the top of the plunger form a container into which the substance can be poured. In 1130, the substance is cast into the sleeve and on top of the plunger. After the substance is cast into the sleeve, the substance gradually approaches room temperature and becomes more solid. In 1140, the sleeve is removed, leaving the substance on the top surface of the plunger. In 1150, the substance and plunger are inserted into a dispensing chamber housing. The injection device is now pre-dosed and ready for use. When the substance is a drug for treating a condition of the eye, a precise dosage can be cast into the sleeve under sterile conditions at a manufacturing site. The pre-dosed injection device (with a precise dosage) can then be put in a sterile pack for shipment. Such a manufacturing process provides for accurate dosing of difficult substances in a controlled environment.

From the above, it may be appreciated that the present invention provides an improved system and method for delivering precise volumes of a substance. The present invention provides an injection device into which a drug is cast. The drug may be heated or cooled (as the case may be) to transform it into a more liquid state that is suitable for casting into a dispensing chamber or onto a plunger. The present invention is illustrated herein by example, and various modifications may be made by a person of ordinary skill in the art.

While described in terms of an ophthalmic injection device, the present invention is suitable for use in any type of injection device. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A dosing assembly comprising:
a plunger having a top and bottom surface;
a removable, hinged sleeve having an interior and exterior surface, the sleeve fitting over the top surface of the plunger, the interior surface forming a mold into which a substance is cast onto the top surface of the plunger; and
the cast substance located on the top surface of the plunger.

2. The dosing assembly of claim 1 wherein the top surface of the plunger is in the form of a shape suitable for receiving the cast substance.

3. The dosing assembly of claim 1 wherein the top surface of the plunger has a texture.

4. The dosing assembly of claim 1 wherein the interior surface of the sleeve is coated.

* * * * *